United States Patent
Fawzy et al.

(10) Patent No.: US 8,163,012 B2
(45) Date of Patent: Apr. 24, 2012

(54) MULTI-PLANAR TRICUSPID ANNULOPLASTY RING

(76) Inventors: Hosam Fouad Fawzy, Toronto (CA); Lee Errett, Toronto (CA); Cyril David Mazer, Toronto (CA); Daniel Bonneau, Grimsby (CA); David Latter, Toronto (CA)

(*) Notice: Subject to any disclaimer, the term of this patent is extended or adjusted under 35 U.S.C. 154(b) by 228 days.

(21) Appl. No.: 12/352,885

(22) Filed: Jan. 13, 2009

(65) Prior Publication Data
US 2010/0179651 A1 Jul. 15, 2010

(51) Int. Cl.
*A61F 2/24* (2006.01)
(52) U.S. Cl. ........... 623/2.36; 623/2.37; 623/2.38
(58) Field of Classification Search ......... 623/2.36–2.38
See application file for complete search history.

(56) References Cited

U.S. PATENT DOCUMENTS

| 5,104,407 A * | 4/1992 | Lam et al. ............. 623/2.36 |
| 5,607,471 A * | 3/1997 | Seguin et al. ......... 623/2.36 |
| 5,716,397 A * | 2/1998 | Myers ................... 623/2.36 |
| 2005/0043791 A1* | 2/2005 | McCarthy et al. ..... 623/2.36 |
| 2007/0100441 A1* | 5/2007 | Kron et al. ........... 623/2.36 |

* cited by examiner

*Primary Examiner* — David H Willse
*Assistant Examiner* — Tiffany Shipmon
(74) *Attorney, Agent, or Firm* — Coats & Bennett, P.L.L.C.

(57) ABSTRACT

A multi-planar annuloplasty ring for implantation adjacent to the tricuspid valve with a gap adjacent to the apex of the triangle of Koch. The anterior part of the ring body extending from the highest point at the anteroseptal commissure down to a lower plane at the anteroposterior commissure. During this course it is curved upwards. The posterior part of the ring body extends downward towards the lowest point at the posteroseptal commissure in a relatively straight course. The septal part of the ring body extending from the lowest point at the posteroseptal commissure upwards towards the highest point at the anteroseptal commissure. During this course it is curved upward.

7 Claims, 5 Drawing Sheets

MULTI-PLANAR TRICUSPID ANNULOPLASTY RING

FIELD OF THE INVENTION

The present invention relates to the field of heart valve repair. More particularly, it relates to the field of the repairing the tricuspid valve.

BACKGROUND OF THE INVENTION

The heart in mammals has four valves that regulate the direction of flow of blood through the four chambers of the heart.

The two atrioventricular valves which prevent the backflow from the ventricles of the heart into the atria and two semilunar valves which prevent backflow from the arteries into the ventricles.

The tricuspid valve is one of the atrioventricular valves and is situated on the right side of the heart between right atrium and the right ventricle. The healthy tricuspid valve generally has three leaflets, three papillary muscles and Chordae Tendineae.

In certain situations, the tricuspid valve can fail to operate partially, fully or at all in a patient. An unhealthy tricuspid valve can cause severe problems to the patient including death as a result of regurgitation of blood through the valve or other problems.

As a result, certain treatments have been developed to address problems with the tricuspid valve. For example in one type of treatment, tricuspid valve surgery, an artificial ring is inserted in to the heart to repair or restore the natural tricuspid valve function.

The natural tricuspid valve changes shape during the course of the cardiac cycle. The shape may be based on the contractions of the papillary muscles, the shape of the leaflets, the shape of the annulus, the supporting chordae and other factors. The tricuspid orifice shows large changes during the cardiac cycle and is easily dilated during the course of disease because of different factors.

The macroscopic structure of the heart may be described as a single muscular band that starts at the base of the pulmonary root and ends at the base of the aortic root. This band forms a basal loop that surrounds the tricuspid and mitral orifices and then descends toward the left ventricular apex in a spiral helix to form the apical loop. Contraction of the basal loop reduces the atrioventricular valve orifices. Therefore, the mobility and size of the tricuspid orifice are largely affected by the transversely oriented myocardial fibers, which surround the atrioventricular valves.

The tricuspid valve is rarely affected in a patient in isolation. Most often, the more prominent impact of other diseased valves minimizes the importance of correcting problems with the tricuspid valve. Since the valve is located near the entrance of the heart, its symptomatology is primarily extracardiac and is often silent making detection and investigation more difficult. In addition, the tricuspid valve's behavior is closely related to the function of the right ventricle. In most cases, tricuspid regurgitation is secondary to right ventricular failure. The valve generally follows the dictates of the mitral valve, so resolution of the mitral problem is often followed by improvement in the degree of tricuspid regurgitation. For these reasons, cardiologists and surgeons often ignore or consider the tricuspid valve as secondary.

Diagnostic and surgical methods for treating functional tricuspid regurgitation have generally followed those applied to the mitral valve. However, the tricuspid valve has features which distinguish it from the mitral valve. It has a tendency to vary in degree following hemodynamic changes which makes evaluation difficult or unreliable.

There are a variety of known techniques for surgical intervention relating to tricuspid valve regurgitation and to restore the tricuspid annular dilation with varying degrees of success. The most common technique is the insertion of a tricuspid annuloplasty ring to help restore and reinforce the tricuspid annulus and consequently minimize the valve regurgitation. It is generally believed that matching the shape of the annuloplasty ring to the natural shape of the tricuspid valve is important to proper function of the ring. The relatively high recurrence rate of tricuspid regurgitation suggests that existing techniques are not fully satisfactory.

Any artificial ring should correspond closely to the shape and properties of the natural tricuspid valve. Recent studies showed high recurrence rate of severe tricuspid regurgitation in patients undergoing variety of tricuspid annuloplasties during mid-term follow up. These results question the efficacy of the current techniques of tricuspid repair.

A tricuspid valve ring is therefore desirable for repair of the tricuspid valve that corresponds closely with the natural valve.

BRIEF DESCRIPTION OF THE DRAWINGS

In drawings which illustrate by way of example only a preferred embodiment of the invention.

DETAILED DESCRIPTION OF THE INVENTION

Figure 1:
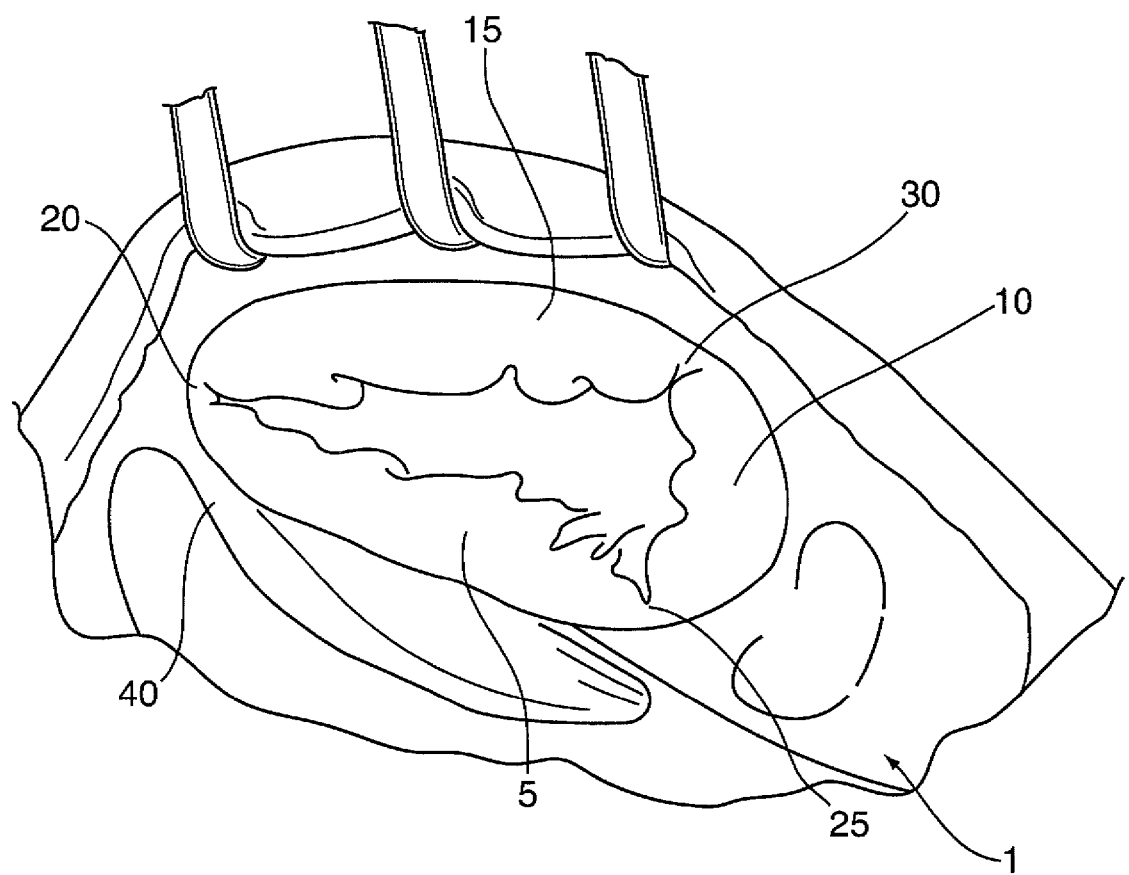
FIG. 1 is a plan view of the normal tricuspid valve.

With reference to FIG. 1, the tricuspid valve 1 is shown with some of the surrounding anatomy. The valve 1 generally consists of three leaflets: the septal 5, posterior 10 and anterior 15 leaflets with the adjoining annular tissue referred to also as septal, posterior and anterior. The three leaflets project in to the flow orifice.

The movement of the leaflets are controlled by papillary muscles (not shown) in the right ventricle which are connected to the leaflets by chordae tendinae. The anterior 15 and posterior 10 leaflets are attached to the free wall of the right ventricle while the septal leaflet 5 is attached to the base of the interventricular septum.

Between the leafets are three commissures: an anteroseptal commissure 20, a posteroseptal commissure 25, and an anteroposterior commissure 30.

Without being limited by theory, the annulus of the tricuspid valve 1 is not in a single plane but has a multiplanar three-dimensional shape with its highest point at the antersептal commissure 20 and its lowest point at the posteroseptal commissure 25 while the anteroposterior commissure 30 lies in a plane in between the other two commissures.

The contractions of the heart are controlled by electrical signals which pass through the conduction tissue. Near the tricuspid valve is the triangle of Koch (TOK) 40, a region which is sensitive for the electrical transmission. The surgeon generally tries to avoid affecting this area of the heart to avoid subsequent heart block.

Figure 2:
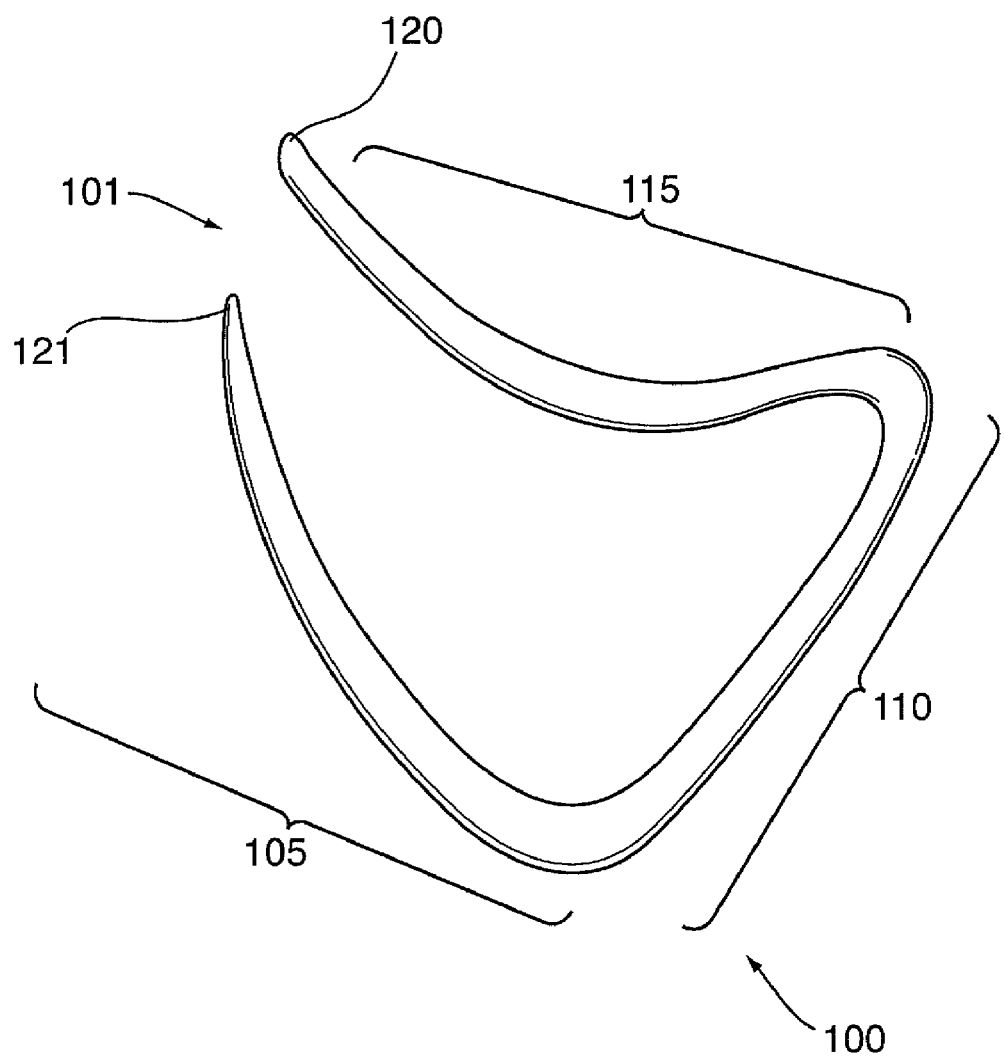
FIG. 2 is a postero-lateral view of an embodiment of the invention.

With reference to FIG. 2, an embodiment of the invention provides an annuloplasty ring 100 which includes a ring body which is not a complete ring but has an opening or gap 101 between the free ends 120, 121. The overall dimensions of the ring 100 may be based on the size of the tricuspid annulus of the patient.

Figure 3:
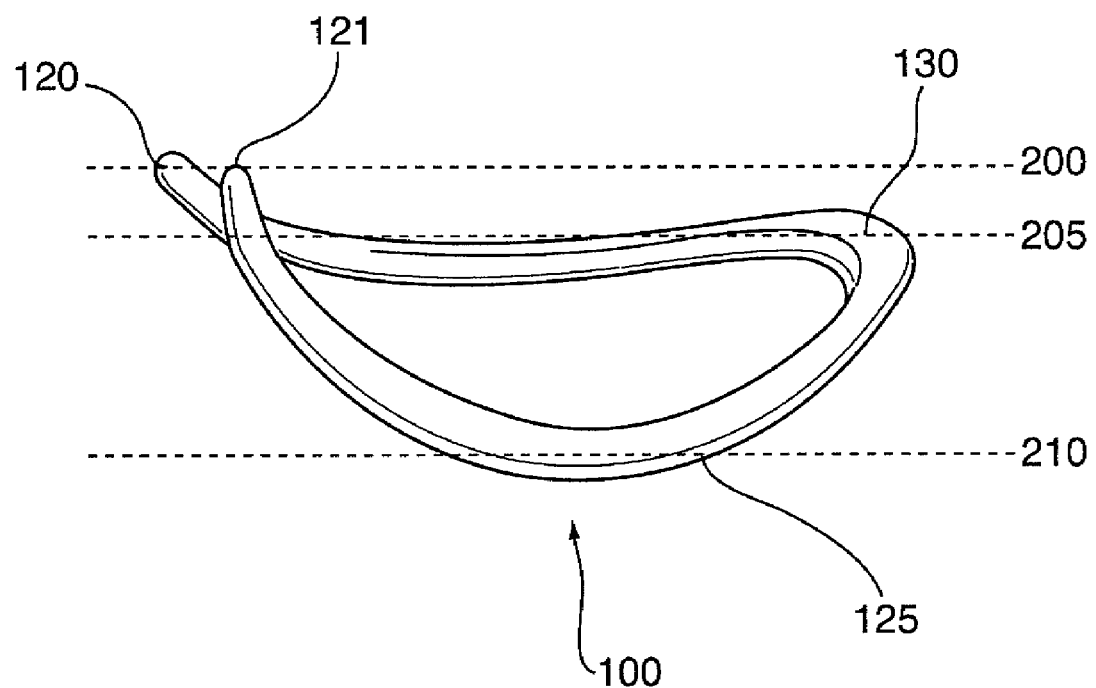
FIG. 3 is a lateral view of an embodiment of the invention.
Figure 4:
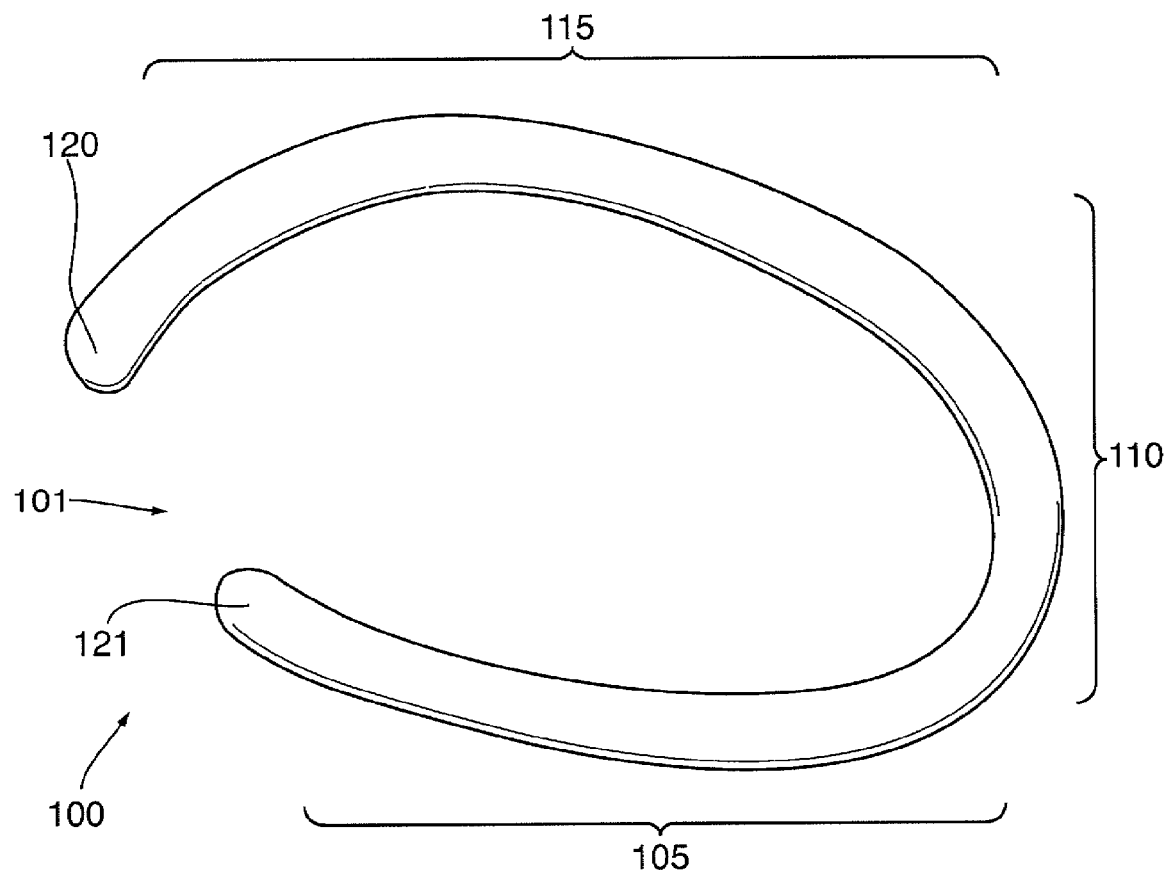
FIG. 4 is a top view of an embodiment of the invention.
Figure 5:
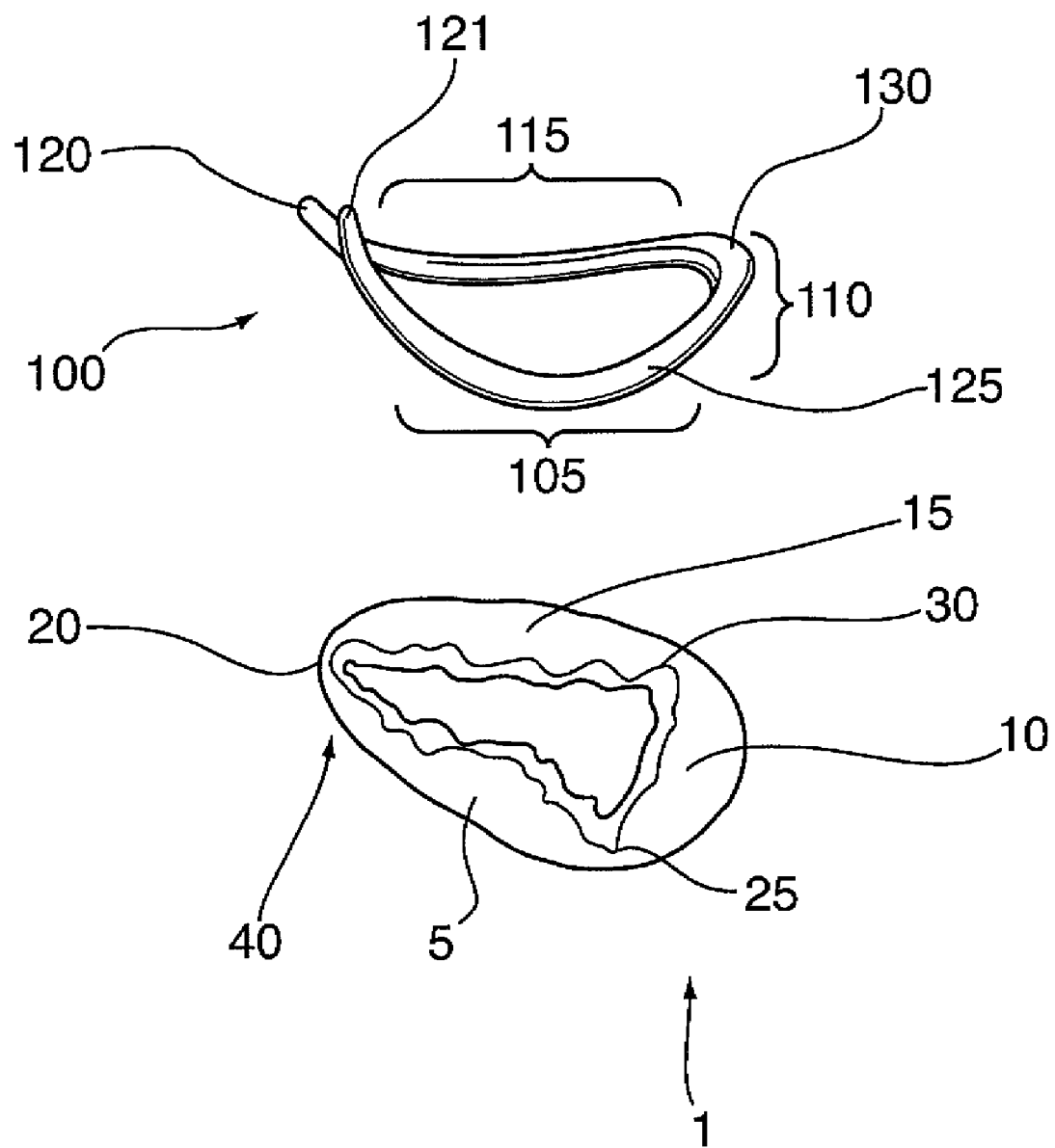
FIG. 5 represents a method of implanting an embodiment of the invention on the tricuspid valve.

The ring 100 has a multi-planar three-dimensional shape. The shape of the ring will be described in relation to the parts of the annulus, commissures and tricuspid valve 1 adjacent to the ring 100. With reference to FIGS. 3 and 5, when placed next to the tricuspid valve, the highest point of the ring 120 aligns with the anterseptal commissure 20 and its lowest point 125 at the posteroseptal commissure 25 while point 130 of the ring adjacent the anteroposterior commissure 30 lies on an imaginary plane 205 between a first imaginary plane 200 intersecting the ring near the anterseptal commissures 20 and a second parallel imaginary plane 210 intersecting the ring adjacent the posteroseptal commissure 25 The point 130 of the ring on the imaginary plane 205 near the anteroposterior commissure 30 may not be exactly positioned between the two planes but is positioned between the planes 200, 210 intersecting the ring near the anterseptal commissure 20 and posteroseptal commissure 25. The imaginary plane 205 is preferably positioned between 0 and 80% of the distance between the first imaginary plane 200 and the second imaginary plane 210.

The ring 100 may also be described in terms of three adjoining and continuous portions or segments of the ring adjacent to the leaflets of the valve. In this manner, a first segment 115 is adjacent to the anterior leaflet 15 of the tricuspid valve adjoining the first free end 120. A second segment 110 is adjacent to the posterior leaflet 10. A third segment 105 is adjacent to the septal leaflet 5. While the ring 100 may be described as three separate segments, the three segments are preferably continuous with the adjoining segments in a smooth curve and may be made from the same material.

This ring is not a complete circle as it has an opening, or gap, 101, between the two free ends, 120 and 121, near to the anteroseptal commissure 20 corresponding to the conduction area at the apex of the triangle of Koch 40.

The anterior segment of the ring body 115 extends from the highest point 120, intersecting the first plane 200 near the anteroseptal commissure 20 down to a middle plane 205 near the anteroposterior commissure 30. The anterior segment 115 is curved upwards. The posterior part of the ring body 110 extends downward towards the lowest point 125 interesting the lowest plane 210 adjacent to the posteroseptal commissure 25 in a relatively straight course. The septal part of the ring body 105 extending from the lowest point at the posteroseptal commissure 25 upwards towards the highest point at the anteroseptal commissure 20 intersecting the first plane 200 again. During this course it has an upward curve. There is a gap 101 in the ring 100 near the apex of the triangle of Koch 40. There is an opening or gap 101 in the ring between the two free ends 120 and 121 to avoid suturing in the area corresponding to the conduction tissue at the apex of the triangle of Koch 40.

The ring 100 may be made from a semi-rigid material. In a preferred embodiment, the ring is made from a semi-rigid material having a superelastic alloy core with a carobfilm coating. As will be known to someone skilled in the art, the ring 100 should be haemobiocompatible to avoid complications when inserted in the heart. The material preferably has progressive degrees of flexibility along the whole length of the ring from septal through the posterior and anterior segments. In a preferred embodiment, the ring has its lowest flexibility near the septal leaflet, the highest flexibility near the anterior leaflet and medium flexibility near the posterior leaflet. The change in flexibility may be implemented by using different alloy compositions at different portions of the ring or by using different ring thicknesses for different portions of the ring.

In an alternative design, the ring 100 may be made of an alloy. In a further alternative, the ring 100 may be made of titanium alloy which substantially resists distortion when subjected to the stress imparted by the surrounding tissue during the movement of the heart.

The ring 100 may alternatively be made from alternating metal segments and plastic segments with the plastic segments providing additional flexibility. In an alternative design, the ring 100 may be made of the Elgiloy alloy.

The ring 100 may be placed in the heart next to the tricuspid valve. To assist with insertion, the ring may be mounted on a template that has the same general profile as the ring. The template may be made from a rigid material such as plastic or fabric. The ring may be mounted on the template where the sutures are passed though the annulus and the ring then gently lowered into position on the tricuspid annulus where the sutures are tied snugly. Generally, the template contains a handle in the center which is used to extract the template once the ring is positioned on the annulus. The ring may be mounted into a groove on the peripheral edge of the template so that a surgeon can pass the suturing material through the mounted ring and then help seat the ring down on the tricuspid annulus.

Various embodiments of the present invention having been thus described in detail by way of example, it will be apparent to those skilled in the art that variations and modifications may be made without departing from the invention. The invention includes all such variations and modifications as fall within the scope of the appended claims.

We claim:

1. An annuloplasty ring for implanting adjacent to the annulus of a tricuspid valve, the valve comprising anterior, posterior and septal leaflets and the annulus comprising an anteroseptal commissure between the anterior and septal leaflets, a posteroseptal commissure between the posterior and septal leaflets, an anteroposterior commissure between the anterior and posterior leaflets, an anterior annular portion adjacent to the anterior leaflet, a posterior annular portion adjacent to the posterior leaflet, and a septal annular portion adjacent to the septal leaflet, with blood flowing in a downward direction though the valve, the ring comprising:
   a first segment for implantation adjacent to the anterior annular portion curved away from a bottom plane, having
      a first free end for implantation adjacent to the anteroseptal commissure of the annulus and intersecting a top plane, and
      a second end for implantation adjacent to the anteroposterior commissure of the annulus and intersecting a middle plane parallel to the top plane,
   a second segment for implantation adjacent to the posterior annular portion, continuous at a first end with the second end of the first segment, having a second end for implantation adjacent to the posteroseptal commissure and intersecting the bottom plane parallel to the top and middle planes;
   a third segment for implantation adjacent to the septal annular portion curved away from the bottom plane, continuous at a first end with the second end of the second segment, having a second free end for implantation adjacent to the anteroseptal commissure of the annulus and intersecting with the top plane;
   whereby the top plane is offset above the middle plane, the bottom plane is offset below the middle plane as oriented by the flow of the blood, the ring has a gap between the first free end of the first segment and second free end of the third segment and, the ring may be implanted adjacent to a tricuspid valve.

2. The ring of claim 1 wherein the gap between the first free end of the first segment and second free end of the third segment are adjacent to the apex of triangle of Koch of the annulus.

3. The ring of claim 1 wherein the second segment is substantially straight.

4. The ring of claim 1 whereby the ring may be attached to the annulus without tension or distortion to the valve.

5. The ring of claim 1 wherein the first, second and third segments are made from a semi-rigid material.

6. The ring of claim 5 wherein the ring is most rigid in the third segment and least rigid in the first segment and the rigidity of the ring progresses between the first segment and the third segment.

7. The ring of claim 1 wherein the first, second and third segment are made from a metal alloy.

* * * * *